US011335457B1

(12) United States Patent
Brown et al.

(10) Patent No.: US 11,335,457 B1
(45) Date of Patent: May 17, 2022

(54) SYSTEM AND METHOD FOR MANAGING EN ROUTE CARE PLATFORM PATIENT LOAD PLANNING AND CARE

(71) Applicant: Government of the United States as represented by the Secretary of the Air Force, Wright-Patterson AFB, OH (US)

(72) Inventors: Kayla N. Brown, Hillsboro, OH (US); Melissa A. Wilson, Hillsboro, OH (US); Brittany L. Fouts, Fairborn, OH (US)

(73) Assignee: United States of America as represented by the Secretary of the Air Force, Wright-Patterson AFB, OH (US)

( * ) Notice: Subject to any disclaimer, the term of this patent is extended or adjusted under 35 U.S.C. 154(b) by 217 days.

(21) Appl. No.: 16/710,030

(22) Filed: Dec. 11, 2019

(51) Int. Cl.
*G16H 40/20* (2018.01)
*G16H 40/67* (2018.01)
*G16H 10/60* (2018.01)

(52) U.S. Cl.
CPC .............. *G16H 40/20* (2018.01); *G16H 10/60* (2018.01); *G16H 40/67* (2018.01)

(58) Field of Classification Search
CPC ......... G16H 40/20; G16H 40/67; G16H 10/60
USPC ........................................................ 705/2–3
See application file for complete search history.

(56) References Cited

U.S. PATENT DOCUMENTS

| 7,899,687 | B2 * | 3/2011 | Morris | G16H 50/80 705/3 |
| 8,040,246 | B2 * | 10/2011 | Graves | A61B 5/681 340/573.1 |
| 2005/0283382 | A1 * | 12/2005 | Donoghue | G16H 40/20 705/2 |
| 2006/0100908 | A1 * | 5/2006 | Becker | G06Q 99/00 705/3 |
| 2008/0250559 | A1 * | 10/2008 | Janboecke | B64D 11/00 5/2.1 |
| 2009/0143045 | A1 * | 6/2009 | Graves | A61B 5/1113 455/404.1 |
| 2009/0164236 | A1 * | 6/2009 | Gounares | G16H 40/20 705/2 |
| 2009/0198733 | A1 * | 8/2009 | Gounares | G16Z 99/00 |
| 2011/0130636 | A1 | 6/2011 | Daniel et al. | |
| 2015/0242577 | A1 * | 8/2015 | Konoske | G16H 20/40 705/2 |
| 2016/0029890 | A1 | 2/2016 | Stump et al. | |

(Continued)

OTHER PUBLICATIONS

Fouts B, Serres J, Hill R, Ciarallo F. (2018). Application Development for Optimizing Patient Placement on Aeromedical Evacuation Flights: Proof-of-Concept. AFRL-SA-WP-SR-2018-0001. US Air Force School of Aerospace Medicine, Aeromedical Research Department, Wright-Patterson AFB, OH. (Technical Report).

(Continued)

*Primary Examiner* — Michael Tomaszewski
(74) *Attorney, Agent, or Firm* — AFMCLO/JAZ; Matthew D Fair (57) ABSTRACT

Various embodiments of the disclosed subject matter provide systems, methods, architectures, mechanisms, apparatus and/or computer implemented method configured for automatically managing En Route Care (ERC) transport patient and medical equipment loading.

19 Claims, 8 Drawing Sheets

(56) References Cited

U.S. PATENT DOCUMENTS

2016/0162641 A1* 6/2016 Ueda .................... G16H 10/60
705/3
2018/0315298 A1* 11/2018 Kitamura ............ G08B 25/014

OTHER PUBLICATIONS

Fouts B, Serres J, Hill R, Ciarallo F. (2016). Application Development for Optimizing Patient Placement in the En Route Care Environment. Aerospace Medicine and Human Performance, 87(3), 198. (Abstract).

Fouts B. Description of Medical Technologies for the Aeromedical Evacuation Environment. Airlift Tanker Association and Air Mobility Command Symposium; Oct. 28-Nov. 1, 2015; Orlando, FL. (Podium).

Fouts B. Role of Dynamic Environments on Medical Care and Patient Monitoring. Semicon West; Jul. 10-12, 2018 San Francisco, CA. (Panel).

Hicks J, Serres J, Fouts B, Hill R, Ciarallo F. Application Development for Optimizing Patient Placement on the C-17 Airframe: Summary of Current Practices. Health and Human Performance Research Summit; Apr. 28-30, 2015; Dayton, OH. (Poster).

Losekamp T, Roseboro J, Fouts B, Bevington D, Wilson M. Mobile Health Apps for En Route Care: A Collaboration between United States Air Force and the Defense Health Agency. International Meeting on Simulation in Healthcare; Jan. 14-17, 2018; Los Angeles, CA. (Podium).

Watson, "Load", Airline Operations Group—Solutions—Smart4Aviation, https://www.smart4aviation.aero/load, Jul. 25, 2019.

* cited by examiner

FIG. 5D

SYSTEM AND METHOD FOR MANAGING EN ROUTE CARE PLATFORM PATIENT LOAD PLANNING AND CARE

GOVERNMENT INTEREST

The invention described herein may be manufactured and used by or for the Government of the United States for all governmental purposes without the payment of any royalty.

FIELD OF THE DISCLOSURE

The present disclosure relates generally to En Route Care (ERC) management and, more particularly, to electronic management of patient loading on transport platforms and related medical resource allocation.

BACKGROUND

This section is intended to introduce the reader to various aspects of art, which may be related to various aspects of the present invention that are described and/or claimed below. This discussion is believed to be helpful in providing the reader with background information to facilitate a better understanding of the various aspects of the present invention. Accordingly, it should be understood that these statements are to be read in this light, and not as admissions of prior art.

A critical factor during En Route Care (ERC) mission planning, such as aeromedical evacuation (AE), mission planning is patient placement within the transport platform. ERC personnel create a patient positioning plan in accordance with various physical and environmental factors, such as patient type (e.g., litter or ambulatory), injury/illness, acuity, destination and so on. Utilizing their clinical and flight expertise, ERC personnel assign each patient a litter location or seat. ERC personnel also have to include seat assignments for the ERC personnel such as flight crew, medical crew/providers, non-medical attendees, and any additional passengers.

Currently, ERC personnel create hand-written patient plans manually during ground mission planning operations. This process is dynamic requiring last minute changes or repeated edits depending on patient status, additional passengers, mission delays, or other unforeseen events. This paper-based positioning plan is distributed to the ERC crew (by hand), the contingency aeromedical staging facility (CASF), and patient movement requirements center (PMRC) (via email of scanned copy). Further, plans are not stored, reused, or evaluated after completion of the mission.

SUMMARY OF THE INVENTION

Various deficiencies in the prior art are addressed below by the disclosed systems, methods, architectures, mechanisms, apparatus and/or computer implemented method configured for automatically managing En Route Care (ERC) transport patient and medical equipment loading.

According to one embodiment, a method for automatically managing En Route Care (ERC) transport patient and medical equipment loading, comprises: transmitting, toward a load manager communications device (LMCD) associated with an ERC transport platform, a corresponding initial transport platform profile defining available transport platform resources and allocations thereof; in response to an LMCD message indicative of a patient selection, identifying transport platform resources for the selected patient and transmitting toward the LMCD a message indicative of the identified medical resources; in response to an LMCD message indicative of a loading plan update, updating the respective current transport platform profile; and transmitting, toward the LMCD associated with the ERC transport platform, a corresponding current transport platform profile defining available transport platform resources and allocations thereof in accordance with the current patient loading plan; wherein each transport platform profile transmitted toward a respective LMCD is configured to be modified by the respective LMCD to update thereby a loading plan. In various embodiments, identifying transport platform resources for the selected patient comprises examining a respective patient profile to identify therefrom at least one continuous use resource critical for survival of the selected patient.

Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

DETAILED DESCRIPTION OF THE INVENTION

The following description and drawings merely illustrate the principles of the invention. It will thus be appreciated that those skilled in the art will be able to devise various arrangements that, although not explicitly described or shown herein, embody the principles of the invention and are included within its scope. Furthermore, all examples recited herein are principally intended expressly to be only for illustrative purposes to aid the reader in understanding the principles of the invention and the concepts contributed by the inventor(s) to furthering the art and are to be construed as being without limitation to such specifically recited examples and conditions. Additionally, the term, "or," as used herein, refers to a non-exclusive or, unless otherwise indicated (e.g., "or else" or "or in the alternative"). Also, the various embodiments described herein are not necessarily mutually exclusive, as some embodiments can be combined with one or more other embodiments to form new embodiments.

The numerous innovative teachings of the present application will be described with particular reference to the presently preferred exemplary embodiments. However, it should be understood that this class of embodiments provides only a few examples of the many advantageous uses of the innovative teachings herein. In general, statements made in the specification of the present application do not necessarily limit any of the various claimed inventions. Moreover, some statements may apply to some inventive features but not to others. Those skilled in the art and informed by the teachings herein will realize that the invention is also applicable to various other technical areas or embodiments, such as patient placement in civilian medical facilities, and logistical planning for senior living centers.

Various embodiments described herein provide a system, method, apparatus and mechanisms supporting a user-friendly interactive tool to aid ERC personnel in the streamlined development of a patient positioning plan and allow electronic transmission of the latest plan such as to AE crewmembers, contingency aeromedical staging facility (CASF) personnel, a patient movement requirements center (PMRC) and potential electronic health record repositories. In addition to providing electronic documentation of patient, passenger, and equipment locations, various embodiments incorporate clinical decision support to assist the positioning plan developer so as to improve patient safety and/or pain management by ensuring a patient is placed in an optimal position for his/her condition. The various embodiments provide a user-friendly interactive tool for positioning plan development suitable for use by ERC providers and mission planners. Thus, the various embodiments provide a process to develop patient load plans by providing an interactive electronic process for developing, saving, and disseminating load plans.

The various embodiments provide a system and method enabling ERC providers to quickly develop patient load plans (i.e., a load plan to identify where patients will be located in an airframe during the flight) and related equipment load plans. The embodiments are configured to update plans in response to changing patient status, addition of new patients, changes in available equipment, or changes in mission priority.

Profile information for the platform, equipment and the like as well as patient information is updated continually to local (e.g., within an airframe or other ERC transport platform) and/or remote servers. The various embodiments provide an interactive electronic process for developing, saving, and disseminating load plans.

The embodiments use a default template for each airframe that, illustratively, "pops up" via a graphical user interface to enable users such as load managers to select from a drop-down menu of available resources/equipment and to place such resources/equipment throughout the airframe, where the airframe can accommodate such equipment (e.g. a patient who needs oxygen, needs to be placed near an oxygen source on the airframe). Users are then able to input patient names and data and then drag and drop where they want the patients to be placed. Users are able to save load plans for future use.

The various embodiments enable rapid and automatic generation of transport platform load plans based on patient needs as indicated by automatic or semiautomatic triage of patients, types of injuries, healthcare provider access to treat, patient mobility and so on. Various databases are updated/synchronized as needed, including transport type, availability, inventory of medical equipment/capability and so on. Various embodiments provide a mechanism for tracking patients within the platform during flight, updating electronic health (e-health) records and the like to help with in-flight clinical decision support and other functions.

Generally speaking, ERC personnel create a load plan including a patient positioning plan in accordance with various physical and environmental factors, such as patient type (e.g., litter or ambulatory), injury/illness, acuity, destination and so on. Patient profile data is used to determine at least an initial patient position and medical resource allocation as part of a load plan being created for a particular transport platform (e.g., C-130H, C-17, and the like), where the platform itself has a profile indicating resource inventory and location, patient locations of varying types (e.g., litter, reclined seat, standard seat, critical care location, non-critical care location and the like) and so on. The various embodiments contemplate automatic determinations of patient location and medical resource allocations with opportunities for load manager override of such determinations and automatic determinations of error or warning conditions associated with boundary condition violations (e.g., improper patient location and/or medical resource allocation where patient care or survivability may be impacted). In addition to the patient location and medical resource allocation functions performed by the various embodiments, optional embodiments also support determining seat assignments for the flight crew, ERC medical providers/crew, non-medical attendees, and additional passengers.

It will be appreciated that the various embodiments described herein with respect to airlift resources and ERC for AE missions are also applicable to sea and ground transport resources and respective ERC missions. In particular, the various embodiments provide for rapid loading of transport resources such as encountered in dynamic ERC situations associated with supporting humanitarian efforts.

Figure 1:
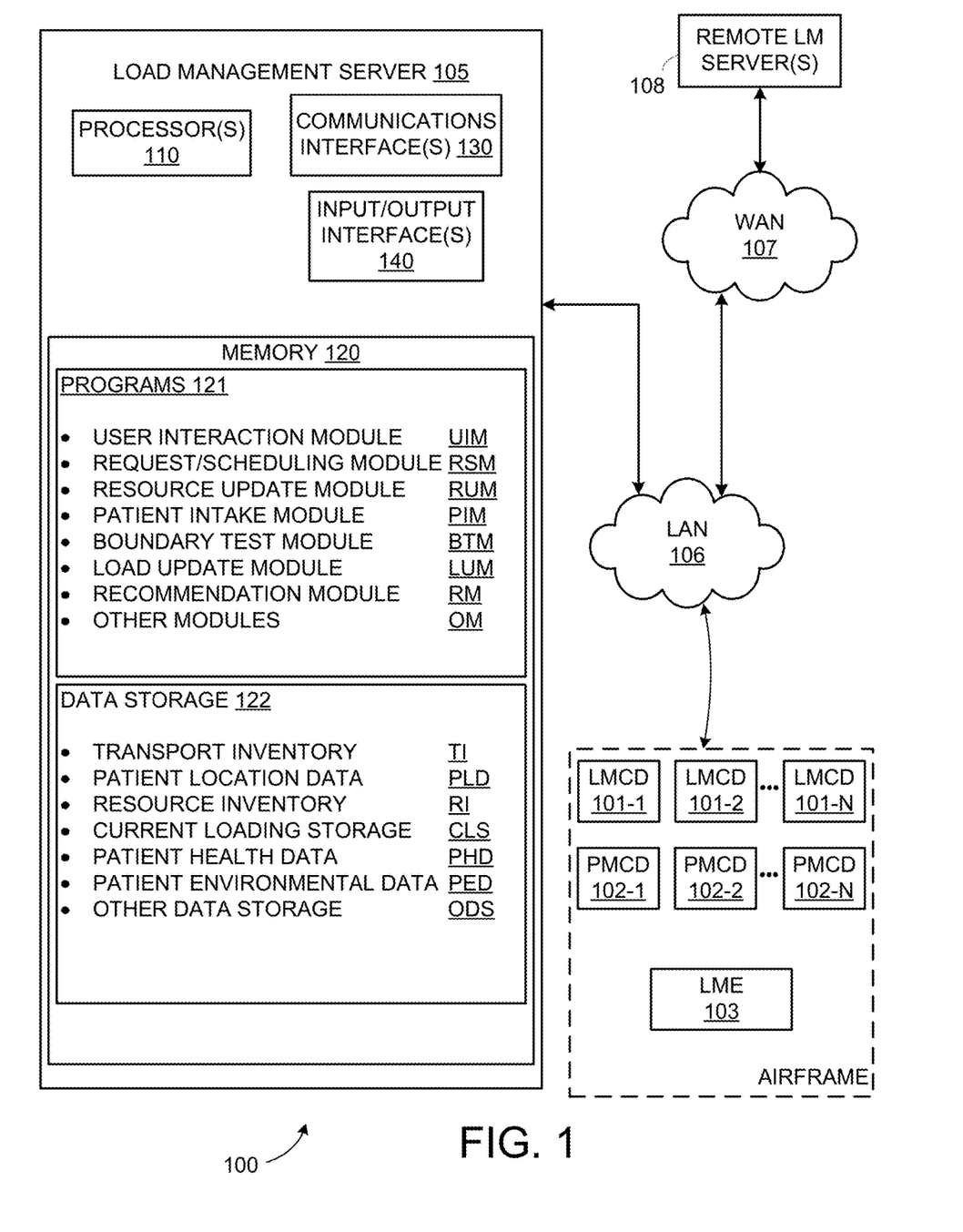
FIG. 1 depicts a high-level block diagram of a load management system according to an embodiment.

FIG. 1 depicts a high-level block diagram of a load management system according to an embodiment. Specifically, the exemplary load management system 100 includes a load management server (LMS) 105 in communication with one or more load manager communications devices (LMCDs) 101 and, optionally, patient monitoring or communications devices (PMCDs) 102, either directly or via a load management entity (LME) 103 or other management entity (not shown), such as a server or scheduler computer associated with an medical evacuation or ERC transport platform, such as an airlift resource for an ERC or AE mission.

Specifically, each load manager (LM) tasked with generating a load plan for an ERC mission may have a respective LMCD 101 comprising a wireless device such as a mobile phone, tablet computer, laptop computers and the like by which the LM may interact with the system to perform various patient intake/selection and resource allocation as described herein. It is noted that one or more load managers may be used to generate or manage a load plan for a single transport platform. Similarly, load plans for multiple transport platforms may be generated or managed at the same time.

As depicted in FIG. 1, the LMS 105 communicates with the LMCDs 101 and optional PMCDs 102 via a local area network 106, illustratively a WiFi hotspot supporting a suitable LAN protocol. It will be appreciated that the communications infrastructure may comprise other technologies depending on distance, environmental factors and the like as is known to those skilled in the art (e.g., Bluetooth, 802.11x, WiFi, WiMAX, 3G, 4G/LTE, 5G etc.).

As further depicted in FIG. 1, the LMS 105 and LMCDs optionally communicates with one or more remote load management servers 108 via a wide area network (WAN) 107 or other access/core network in communication with the LAN 106. Portions of networks 106 or 107 may comprise optical, satellite or other network infrastructure to support back channel communications between LMS 105 and the LMCDs 101.

Optionally, each patient may have one or more respective patient monitoring or communications devices (PMCD) 102 for enabling one or more of patient communications, patient health monitoring, patient environmental monitoring, patient location tracking and/or other patient related functions. Various embodiments contemplate that some PMCDs 102 are capable of supporting multiple patient related functions. Various embodiments contemplate that some PMCDs 102 are used by other ERC personnel, such as medical provider personnel, non-medical personnel, flight crews and the like.

PMCDs 102 enabling communications may comprise a wireless communications device such as a mobile phone, tablet computer, laptop computers and the like by which the patient may interact with the system to provide data, request assistance, consumer still or moving imagery, read reports and so on.

PMCDs 102 enabling health monitoring may comprise any type of patient health monitoring equipment or sensors suitable for monitoring patient health and function, such as integrated or individual patient monitoring equipment for monitoring heart function, brain function (or any other organ function), blood pressure, blood oxygen level, blood chemistry, wound care status and the like, as well as traction/equipment stability and any other factors relevant to patient treatment/safety. Some patient health monitoring functions may be included within, or communicate with, other types of PMCDs 102, such as patient communications devices and the like.

PMCDs 102 enabling environmental monitoring may comprise sensors configured to record environmental factors experienced by a patient, a group of similarly situated patients or other personnel, such as altimeters, pressure sensors, vibration/shock sensors, air quality/composition sensors and so on. Some patient environmental monitoring functions may be included within, or communicate with, other types of PMCDs 102, such as patient communications devices and the like.

PMCDs 102 enabling location monitoring may comprise any type of location monitoring equipment or sensors suitable for monitoring patient (or other personnel) location within and/or outside of an ERC transport platform, such as global position system (GPS) locators, radio frequency (RF) identification tags secured to the patient (e.g., within a patient's wristband) cooperatively coupled to RFID interrogations circuitry within different areas of the ERC transport platform (e.g., fore, aft, specific side, specific row(s), isolation unit, trauma unit etc.), fixed patient locations (e.g., assigned litter or gurney) and so on. Some patient location monitoring functions may be included within, or communicate with, other types of PMCDs 102, such as patient communications devices and the like. Location information may be periodically collected and use to assist medical providers with en route patient care as well as post mission patient care, such as communicable disease response. For example, an LMS 105 may be configured to provide at least a platform location assignment for each ERC patient (optionally, a map of ERC patient movements within the platform during) to a permanent EHR for follow-up, post ERC. In this manner, if a particular patient location or location movements were near an unknown carrier of communicable disease and this disease is not found until post-transport, patient location data and other flight plan data may be used to assist with recognizing those patients that were within the parameters (proximity, physical touching, shared resource usage etc.) of the diseased patient such that the patients at risk may be properly treated without subjecting the entirety of the patient population to such treatment, and without subjecting the entirety of the transport platform to remedial cleaning if such remedial cleaning is unwarranted in portions of the transport platform. Thus, in various embodiments, in response to an indication of an ERC transport platform location being associated with a pathogen or having located therein a patient exhibiting symptoms of a communicable disease, patient location information is used to identify any patients and/or or non-patients exposed to that ERC transport platform location.

The PMCDs 102 enabling environmental monitoring may comprise any type of environmental monitoring equipment or sensors suitable for monitoring environmental conditions impacting patients (or other personnel) such as mechanical stresses and shocks, vibrations and the like, as well as atmospheric changes (oxygen levels, pressure, temperature etc.) to that changes in patient care may be adapted to such conditions. For example, various environmental conditional such as mechanical stresses and shocks, vibrations and the like as well as atmospheric changes (oxygen levels, pressure etc.) are contributors to fatigue. As such, in various embodiments, monitored environmental condition data is used individually or with other information (e.g., sleep levels, hydration levels etc.) to calculate fatigue levels in patients or other personnel such that timely intervention with a fatigued individual may be provided (e.g., move fatigued patient to a lower vibration location, move fatigued nurse to a less active/demanding station etc.) where factors indicative of fatigue beyond a threshold level are present.

Specific hardware implementations associated with the LMS 105 and LMCDs 101 will be discussed in detail. However, a general computing infrastructure such as discussed with respect to the advertising server/updater 105 may be used to implement any of the functions associated with the LMS 105, LMCDs 101, LME 103 and remote LM server(s) 108.

Referring to FIG. 1, the LMS 105 is depicted as including one or more processors 110, a memory 120, one or more communications interfaces 130, and one or more input/output (I/O) interfaces 140. The processor(s) 110 is coupled to each of memory 120, communication interface(s) 130, and I/O interface(s) 140.

The processor(s) 110 is configured for controlling the operation of LMS 105, including operations to interact with LMCDs 101 associated with one or more transport platforms, or respective load management entities 103, as well as performing various calculation/processing functions and the like as described herein.

Generally speaking, the memory 120 may store any information suitable for use by the LMS 105 in implementing one or more of the various methodologies or mechanisms described herein. It will be noted that while various functions are associated with specific programs or databases, there is no requirement that such functions be associated in the specific manner. Thus, any implementations achieving the functions of the various embodiments may be used.

As depicted, the memory 120 is configured for storing programs 121, data 122 and the like. In various embodiments, programs 121 may include one or more programming modules/routines such as, illustratively, a user interaction module UIM, a request/scheduling module RSM, a resource update module RUM, a patient intake module PIM, a boundary test module BTM, a load update module LUM, a recommendation module RM and/or other modules OM. Various modules/routines may be combined as will be discussed in more detail below. In various embodiments, data storage 122 may include one or more databases, file storage mechanisms and the like such as, illustratively, transport inventory TI, patient location data PLD, resource inventory RI, current loading storage CLS and/or other data storage ODS. Optionally, the data storage 122 may include patient health data PHD, patient environmental data PED. The memory 120 may store any other information suitable for use by LMS 105 in providing the various patient care management functions as described herein.

The communications interface(s) 130 include the necessary networking and/or communications capability to enable communications with LAN 106, WAN 107 and/or directly with LMCDs 101 and/or various other entities as discussed herein. It will be appreciated that fewer or more, as well as different, communications interfaces may be supported. The communications interface(s) 130 may include one or more services signaling interfaces such as a Wi-Fi or WiMAX interface, a 3G broadband cellular network wireless interface, a 4G broadband cellular network wireless interface, an Ethernet interface and the like for supporting data/services signaling between tracking and LMS 105/108 and the WAN 107, LAN 106 and/or directly with LMCDs 101 and/or various other entities as discussed herein. It will be appreciated that fewer or more, as well as different, communications interfaces may be supported. The various communications interfaces 130 are adapted to facilitate the transfer of files, data structures, messages, requests and the like between various entities in accordance with the embodiments discussed herein.

The I/O interface 140 may be coupled to one or more presentation devices (not shown) such as associated with display devices for presenting information to a user of the LMS 105/108, one or more input devices (not shown) such as computer touch screen or keypad input devices for enabling user input, and/or interfaces enabling communication between the LMS 105/108 and other computing, networking, presentation or input/output devices (not shown).

Although primarily depicted and described as having specific types and arrangements of components, it will be appreciated that any other suitable types and/or arrangements of components may be used for LMS 105/108.

It will be appreciated that the functions depicted and described herein with respect to the LMS 105 or 108 may be implemented in hardware and/or a combination of hardware and software, e.g., using a general-purpose computer, one or more application specific integrated circuits (ASIC), and/or any other hardware equivalents. In one embodiment, the various programs depicted as loaded within memory 120 are executed by the processor(s) 110 to implement their respective functions. It will also be appreciated that the various programs may be stored on a computer readable storage medium prior to being loaded into memory 120; such computer readable storage media comprising semiconductor memory devices, magnetic media, optical media, electromagnetic media and the like. Generally speaking, any form of tangible and non-transient computer memory may be used to store computer instructions which, when executed by the processor 110, operate to perform the various methods and functions described herein.

It is contemplated that some of the steps discussed herein as software methods may be implemented within hardware, for example, as circuitry that cooperates with the processor to perform various method steps. Portions of the functions/elements described herein may be implemented as a computer program product wherein computer instructions, when processed by a computer, adapt the operation of the computer such that the methods and/or techniques described herein are invoked or otherwise provided. Instructions for invoking the inventive methods may be stored in tangible and non-transient fixed or removable media, transmitted via a data stream in a tangible and non-transient signal-bearing medium, and/or stored within a memory within a computing device operating according to the instructions.

Figure 2:
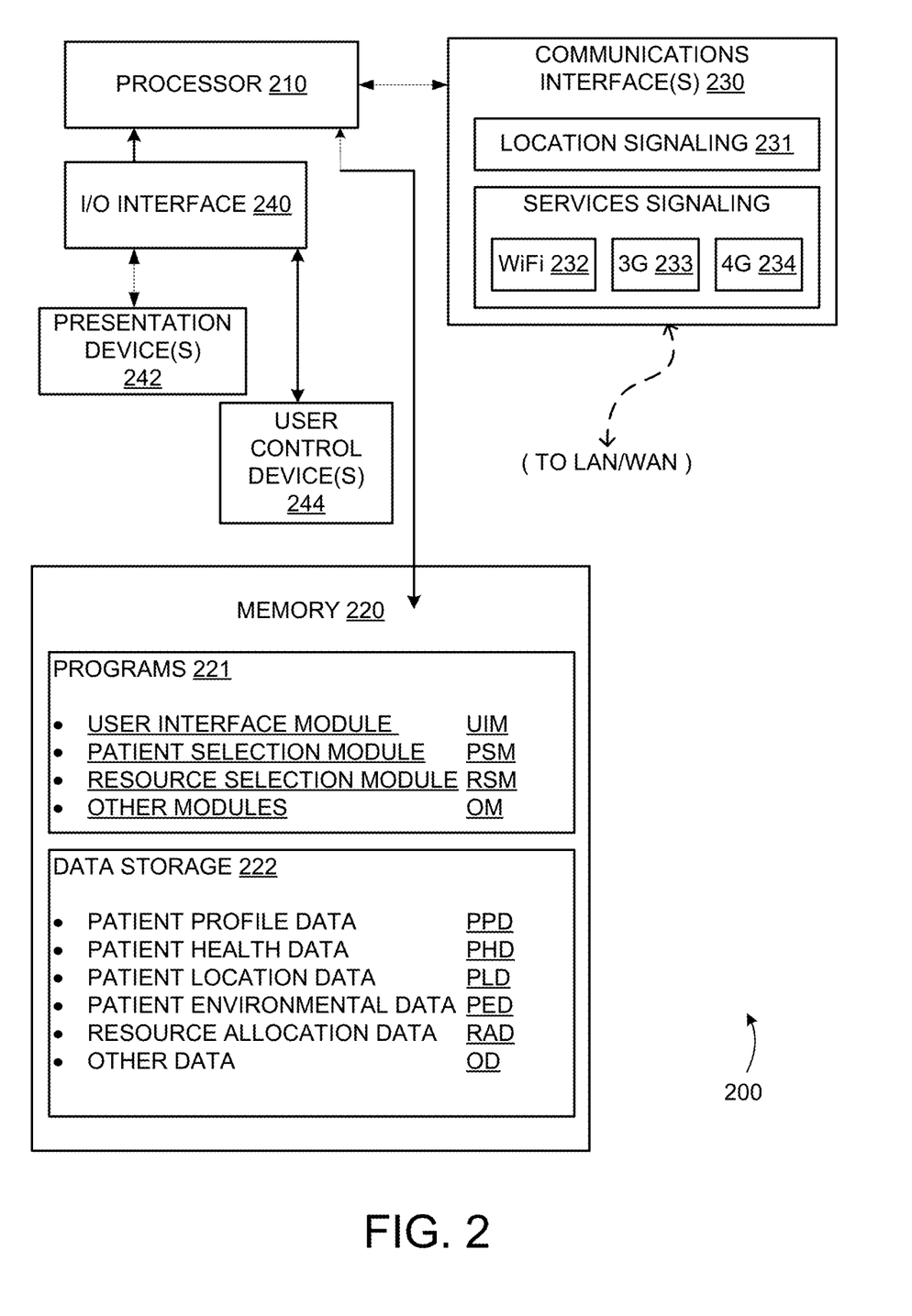
FIG. 2 depicts a high-level block diagram of a load manager communications device (LMCD) suitable for use with the load management system of FIG. 1.

FIG. 2 depicts a high-level block diagram of a load manager communications device (LMCD) suitable for use with the load management system of FIG. 1. Specifically, the LMCD 200 of FIG. 2 may be used to implement the LMCD 101 described herein with respect to FIG. 1. Further, the architecture and various functions described herein with respect to the LMCD 200 of FIG. 2 may be adapted for implementing some or all of the functions described above with respect to the PMCD 102 of FIG. 1.

In various embodiments, the LMCD 200 provides a graphical user interface (GUI) configured to enable user interaction (e.g., such as with a load manager) by, illustratively, displaying a current load plan of a transport resource based upon a graphical representation of the patient location and resources associated with that transport resource via a transport resource profile, such as noted with respect to FIGS. 5A-5D.

As depicted in FIG. 2, the LMCD 200 includes a processor 210, a memory 220, communications interfaces 230, input-output (I/O) interface 240, presentation interface(s) 242, and user control devices 244. The processor 210 is coupled to each of memory 220, communication interfaces 230, and I/O interface 240. The I/O interface 240 is coupled to presentation interface(s) 242 for presenting information on LMCD 200 (e.g., mobile phone display screen, tablet display screen, laptop display and the like) and is coupled to user control interface(s) 244 (e.g., mobile phone touch screen, tablet touch screen, laptop touchscreen or keypad input devices and the like) for enabling user control of LMCD 200.

The processor 210 is configured for controlling the operation of LMCD 200, including operations to provide the advertising presentation and transaction capability.

The memory 220 is configured for storing information suitable for use in providing the advertising presentation and transaction capability. Memory 220 may store programs 221, data 222 and the like.

In one embodiment, programs 221 may include one or more of a user interface module UIM (e.g., a graphical user interface), a patient selection module PSM, a resource selection module RSM and/or other modules OM. In various embodiments, data storage 222 may include one or more of patient profile data PPD, patient health data PHD, patient location data PLD, patient environmental data PED, resource allocation data RAD and/or other data OD. The memory 220 may store any other information suitable for use by LMCD 200 in supporting the various functions described herein with respect to the exemplary load management system.

The communications interfaces 230 may include a location signaling interface such as a global positioning GPS and or cellular telephone tower triangulation system to determine the location of the LMCD 200.

The communications interfaces 230 include one or more services signaling interface such as a Wi-Fi or WiMAX interface 232, a 3G wireless interface 233, and/or a 4G wireless interface 234 for supporting data/services signaling 126 between LMCD 200 and external communications and services infrastructure/network 106. It will be appreciated that fewer or more, as well as different, communications interfaces may be supported.

The I/O interface 240 provides an interface to the presentation device(s) 242 and user control device(s) 244 of LMCD 200.

The presentation device(s) 242 may include a mobile phone, tablet computer or laptop computer display screen, a projector, a printer, one or more speakers, and the like, which may be used for displaying data, displaying video, playing audio, and the like, as well as various combinations thereof. The typical presentation interfaces associated with user devices, including the design and operation of such interfaces, will be understood by one skilled in the art.

The user control device(s) 244 may include any user control interface(s) suitable for use in enabling a user of the LMCD 200 (e.g., a patient) to interact with the LMCD 200 and communicate thereby the LMS 105/108. For example, the user control device(s) 244 may include touch screen-based user controls, stylus-based user controls, a keyboard and/or mouse, voice-based user controls, and the like, as well as various combinations thereof. The typical user control interfaces of user devices, including the design and operation of such interfaces, will be understood by one skilled in the art.

Although primarily depicted and described as having specific types and arrangements of components, it will be appreciated that any other suitable types and/or arrangements of components may be used for LMCD 200. The LMCD 200 may be implemented in any manner suitable for enabling interaction with a load manager such as to select or admit patients to a load plan being formed, locate the patients in a transport platform, allocate resources to the patients and/or for other functions as described herein.

Although primarily depicted and described as having specific types and arrangements of components, it will be appreciated that any other suitable types and/or arrangements of components may be used for LMCD 200.

It will be appreciated that the functions depicted and described herein with respect to the LMCD 200 may be implemented in hardware and/or a combination of hardware and software, e.g., using a general-purpose computer, one or more application specific integrated circuits (ASIC), and/or any other hardware equivalents. In one embodiment, the various programs depicted as loaded within memory 220 are executed by the processor(s) 210 to implement their respective functions. It will also be appreciated that the various programs may be stored on a computer readable storage medium prior to being loaded into memory 220; such computer readable storage media comprising semiconductor memory devices, magnetic media, optical media, electromagnetic media and the like. Generally speaking, any form of tangible and non-transient computer memory may be used to store computer instructions which, when executed by the processor 210, operate to perform the various methods and functions described herein.

It is contemplated that some of the steps discussed herein as software methods may be implemented within hardware, for example, as circuitry that cooperates with the processor to perform various method steps. Portions of the functions/elements described herein may be implemented as a computer program product wherein computer instructions, when processed by a computer, adapt the operation of the computer such that the methods and/or techniques described herein are invoked or otherwise provided. Instructions for invoking the inventive methods may be stored in tangible and non-transient fixed or removable media, transmitted via a data stream in a tangible and non-transient signal-bearing medium, and/or stored within a memory within a computing device operating according to the instructions.

Figure 3:
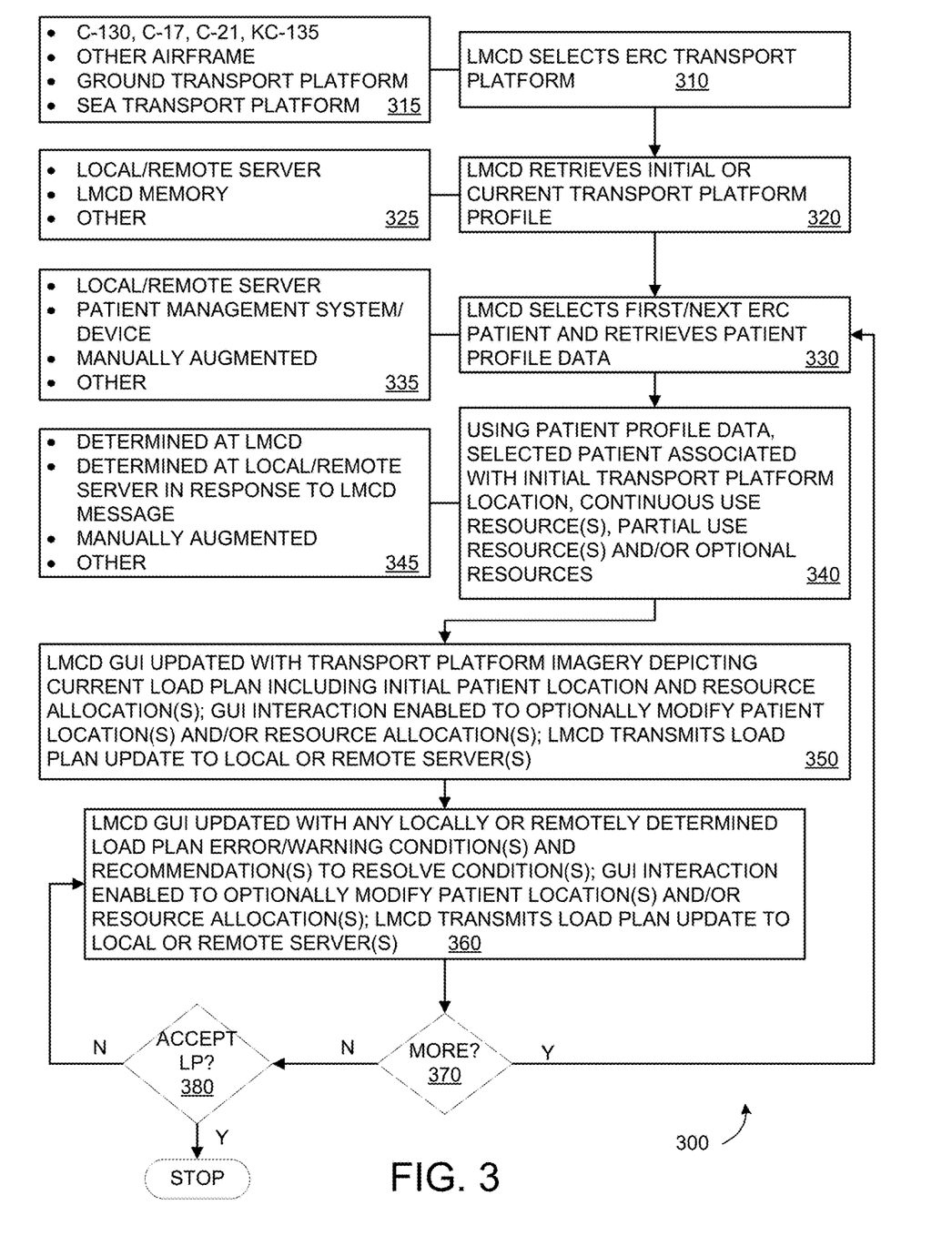
FIG. 3 depicts a flow diagram of a load management method according to an embodiment.

FIG. 3 depicts a flow diagram of a load management method according to an embodiment. In particular, the method 300 is primarily invoked at the LMS 105 (optionally a remote LMS 108 or LME 103) in some embodiments in that commands/messages are transmitted to various LMCDs 101/200 such as associated with each load manager, where the commands/messages cause the LMCDs 101/200 to invoke local functions/programming as described herein. In various other embodiments, the method 300 is primarily invoked at the LMCDs 101/200 that many of the functions are primarily performed locally by the LMCDs, with various levels of function offloading to the LMS 105, remote LMS 108 or LME 103.

Broadly speaking, the LMS 105 interacts with one or more load managers via respective LMCDs 101/200 to automatically generate/update load plans associated with air, ground or sea transport platforms tasked with medical evacuation or ERC missions.

At step 310, an LMCD is used to select an available ERC transport platform, such as (per box 315) and airframe such as a C-130, C-17, C-21, KC-135 or other airframe, a ground transport platform or a sea transport platform. For purposes of this discussion, it will be assumed that an air transport platform is utilized as part of an aeromedical evacuation (AE), mission.

At step 320, the LMCD retrieves an initial or current transport platform profile of the selected transport platform. Referring to box 325, the transport platform profile may be retrieved from a local or remote server, the LMCD memory or some other source. The transport platform profile defines all of the information necessary to construct a load plan associated with the transport platform, such as patient locations, resource locations and so on as described herein. Further, the transport platform profile may also include graphical imagery associated with the platform including patient location imagery, resource location imagery and the like suitable for use within the context of a graphical user interface generated by the LMCD for use by the load manager while forming a load plan.

At step 330, the LMCD selects a first or next ERC patient for processing into the load plan and retrieves the corresponding patient profile data. Referring to box 335, this information may be retrieved from a local or remote server, a patient management system or device and/or other source.

Optionally, the patient profile data may be manually augmented via the load manager or other personnel such as via the LMCD.

At step 340, using the patient profile data the selected patient is associated with an initial transport platform location (e.g., litter position, reclining seat, fixed seat and the like), any appropriate continuous use resources (e.g., fluid deliver resource such as an intravenous delivery device(s), breathing resource such as a ventilator, cardiac monitoring equipment and the like), any appropriate partial use resources (e.g., defibrillators and the like) and or any optional resources (portable ultrasound, secondary medical supplies, medication bags, emergency supplies and so on).

Referring to box 345, processing of the patient profile data to determine recommended location and resource allocation may be performed at the LMCD, at a local or remote server such as in response to an LMCD message or another location. Optionally, the patient profile data may be manually augmented to indicate a preferred location and/or resource allocation. Further, the determined patient location and resource allocation may be manually augmented to prioritize criteria used in the patient location/resource determination.

At step 350, the graphical user interface of the LMCD is updated with transport platform imagery depicting the current load plan including initial patient location and resource allocation(s), such as determined at step 340. Further, GUI interaction is enabled to allow the load manager to optionally modify patient location and/or resource allocation. Further, the LMCD transmits a load plan update message to one or more local or remote servers for further processing.

Such further processing may include, illustratively, determining whether or not a boundary condition associated with a patient location or resource allocation is dangerous or suboptimal. Such further processing may also include determining a recommended resolution to a dangerous, improper or suboptimal patient location or resource allocation. A determination of a dangerous or improper patient location or resource allocation may be made by the LMS 105 and transmitted to the LMCD 101 as part of an error message. A determine of a suboptimal patient location or resource allocation may be made by the LMS 105 and transmitted to the LMCD 101 as part of a warning message. The error/warning messages may optionally include one or more recommendations determined by the LMS 105 as appropriate load plan modifications for resolving the error/warning condition(s). For example, patients with an external fixation device placed on a top litter or a patient in heart failure positioned with their head to the back of the aircraft.

It is noted that the various embodiments are configured to update plans in response to changing patient status, addition of new patients, changes in available equipment, or changes in mission priority. Thus, in various embodiments, LMS 105 operates to continually update such information and proactively transmit error/warning messages as appropriate if boundary conditions and the like are violated in response to such information updates. In this manner, the various embodiments provide an interactive electronic process for developing, saving, and disseminating load plans.

At step 360, the LMCD GUI imagery is further updated to include any locally or remotely determined load plan error/warning condition(s) and corresponding recommendations to resolve such condition(s). Further, GUI interaction is enabled to allow the load manager to optionally modify patient location and/or resource allocation associated with the selected patient or any patient previously processed into the load plan. Further, the LMCD transmits a load plan update message to one or more local or remote servers for further processing.

At step 370, a determination is made as to whether more patients are to be processed into the load plan. If more patients are to be processed, then the method proceeds to step 330 where the patient profile data of the next patient is retrieved. If no more patients are to be processed, then at step 380 a determination is made as to whether the current load plan should be accepted. If the current load plan is acceptable, then the method exits. If the current load plan is not acceptable, then the method proceeds to step 360 where patient location and/or resource allocation may be further modified so as to reduce error conditions, warning conditions and so on.

Figure 4:
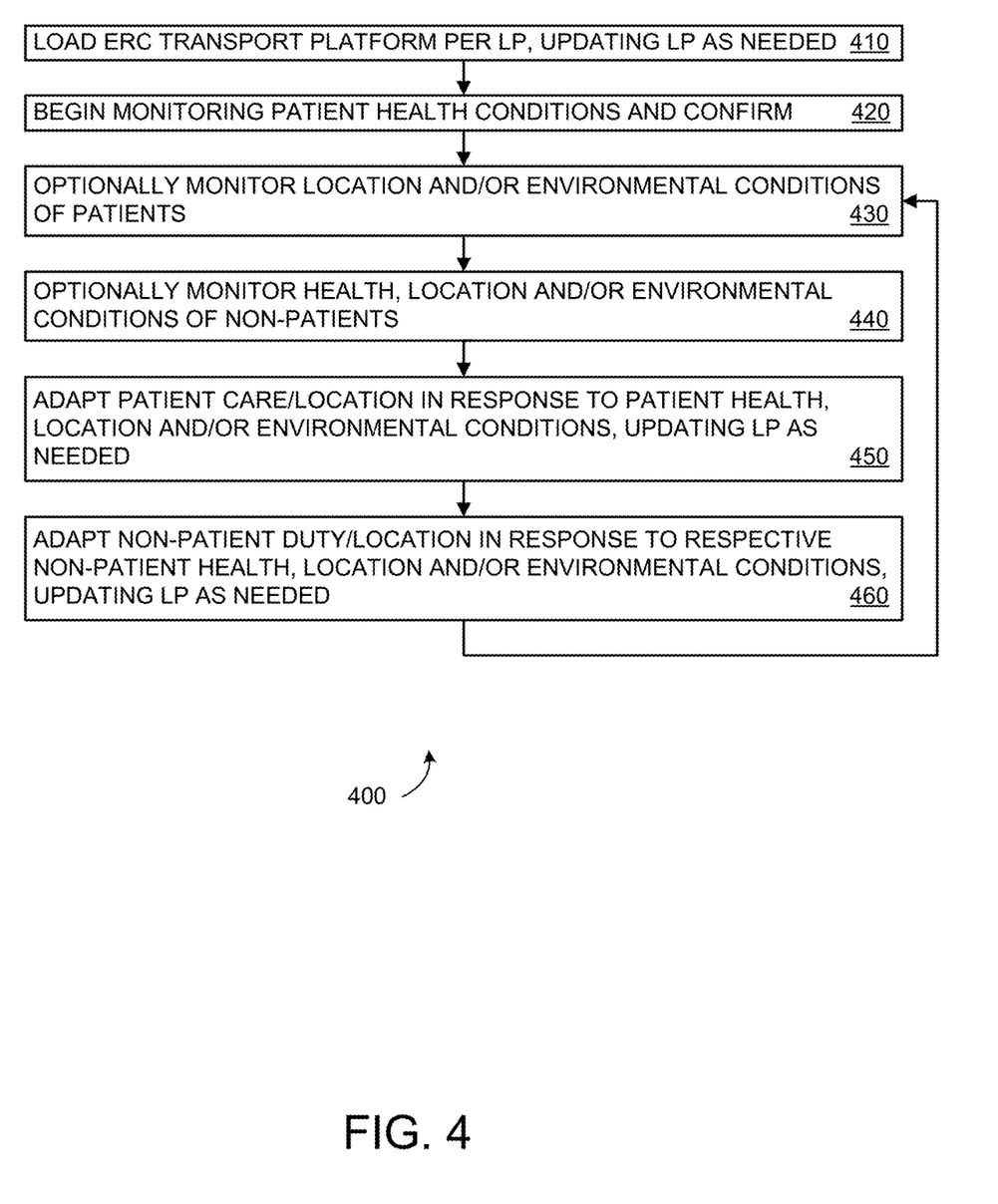
FIG. 4 depicts a flow diagram of a post-load management method according to an embodiment.

FIG. 4 depicts a flow diagram of a post-load management method according to an embodiment. In particular, the method 400 is primarily invoked at the LMS 105 or LME 103 to adapt the load plan in response to monitored patient or non-patient information during transit. Broadly speaking, the LMS 105 interacts with one or more PMCDs 102 to automatically generate/update load plan changes associated with patient or non-patient fatigue, stress, contamination, exposure to communicable diseases or toxins and so on during an ERC mission.

At step 410, the ERC transport platform is loaded with patients and other personnel, and equipment/supplies operative in accordance with a load plan (LP), such as determined above with respect to FIG. 3. The LP is also updated as needed.

At step 420, patient health monitoring is initiated and confirmed as working correctly.

At optional step 430, patient location and/or environmental monitoring is provided.

At optional step 440, non-patient health, location and/or environmental monitoring is provided.

At optional step 450, an alarm or warning indicative of a need to adapt patient care and/or location is generated in response to respective patient health, location and/or environmental monitoring indicative of a condition requiring or suggesting such adaptation. The LP is also updated as needed.

At optional step 460, an alarm or warning indicative of a need to adapt non-patient duty and/or location is generated in response to respective non-patient health, location and/or environmental monitoring indicative of a condition requiring or suggesting such adaptation. The LP is also updated as needed.

The method 400 repeats the monitoring and adapting functions 420-460 periodically or continuously throughout the mission.

Figure 5A:
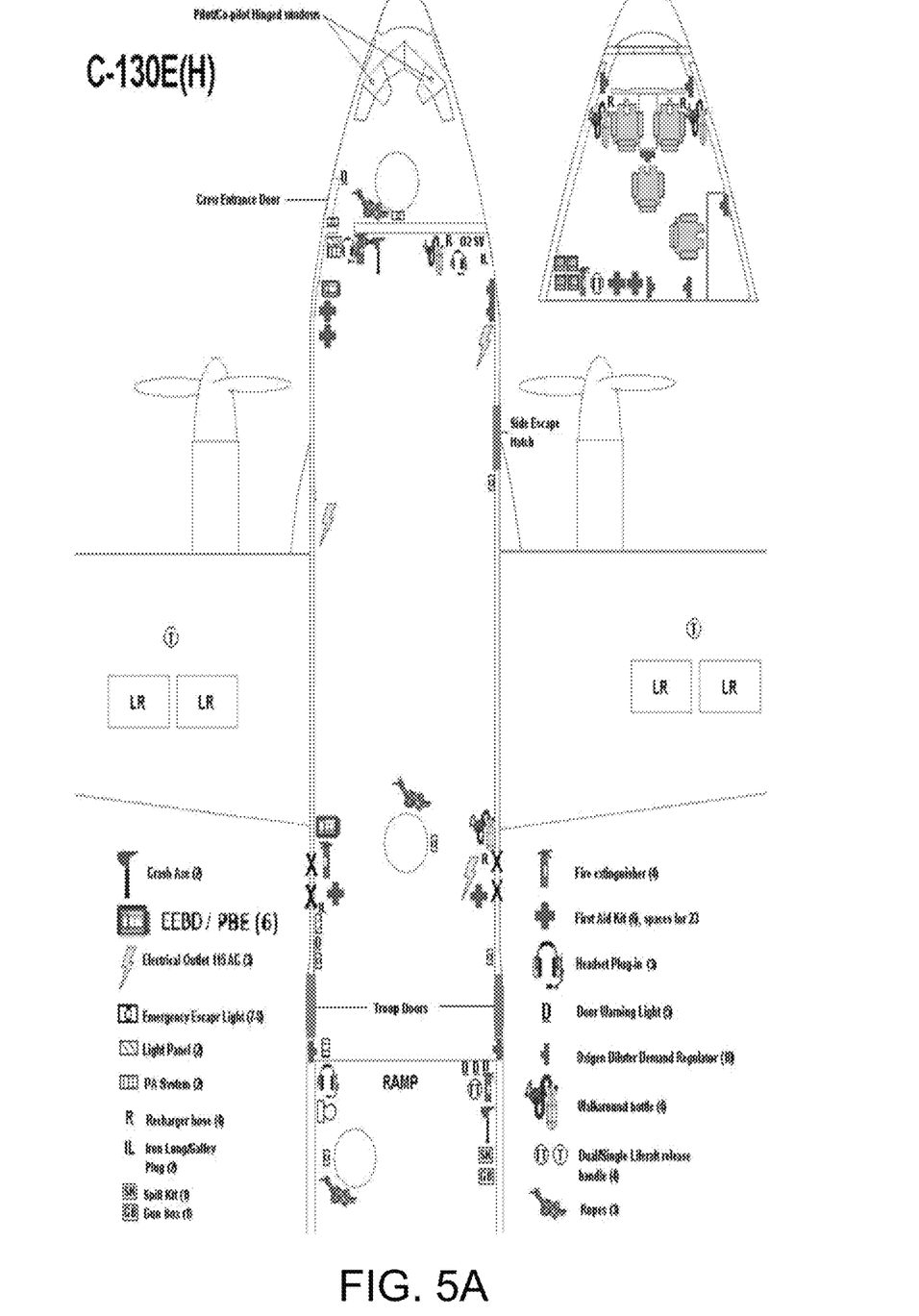
FIGS. 5A-5D depict positioning diagrams for exemplary airframes utilized as airlift resources.
Figure 5B:
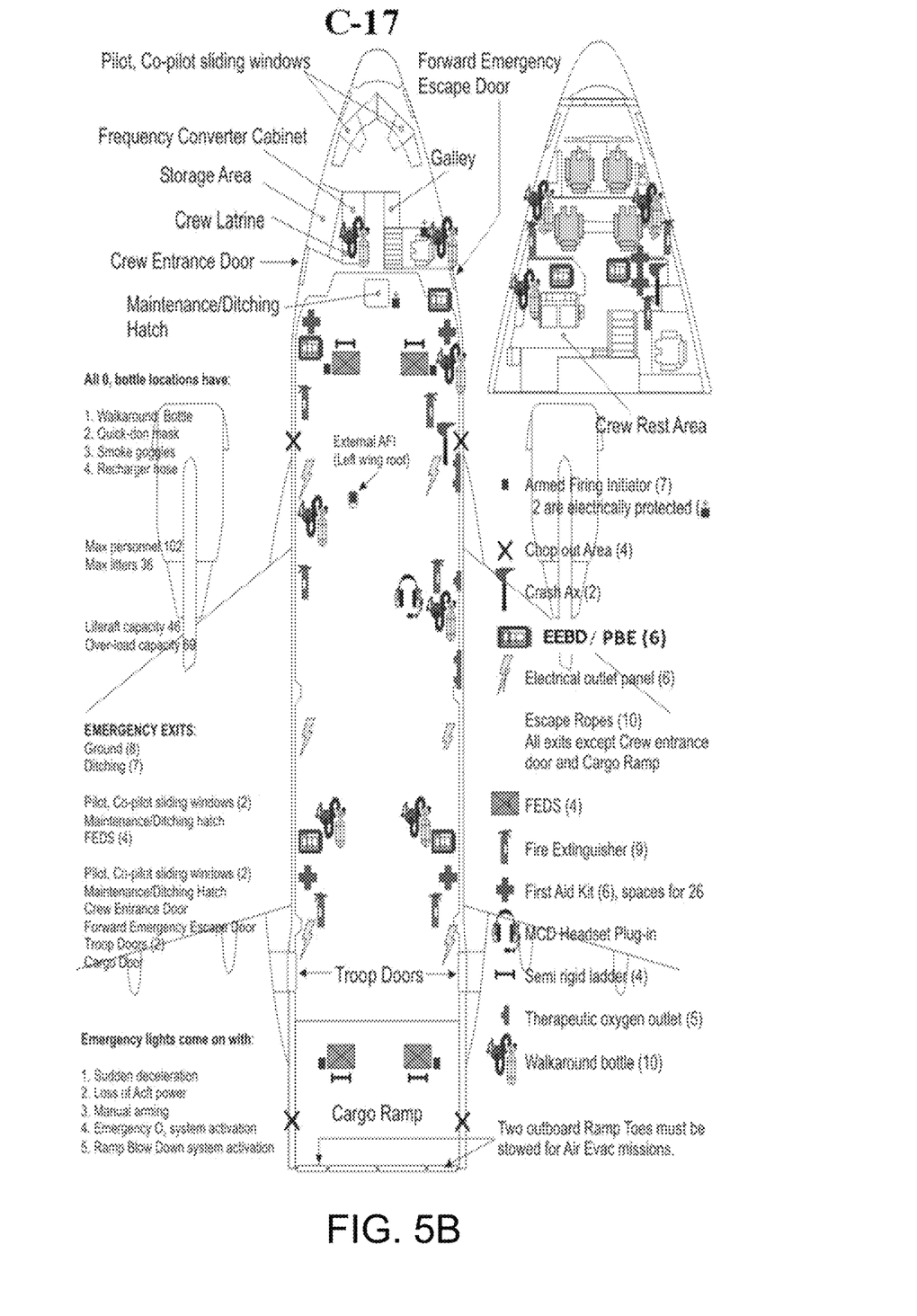
Figure 5C:
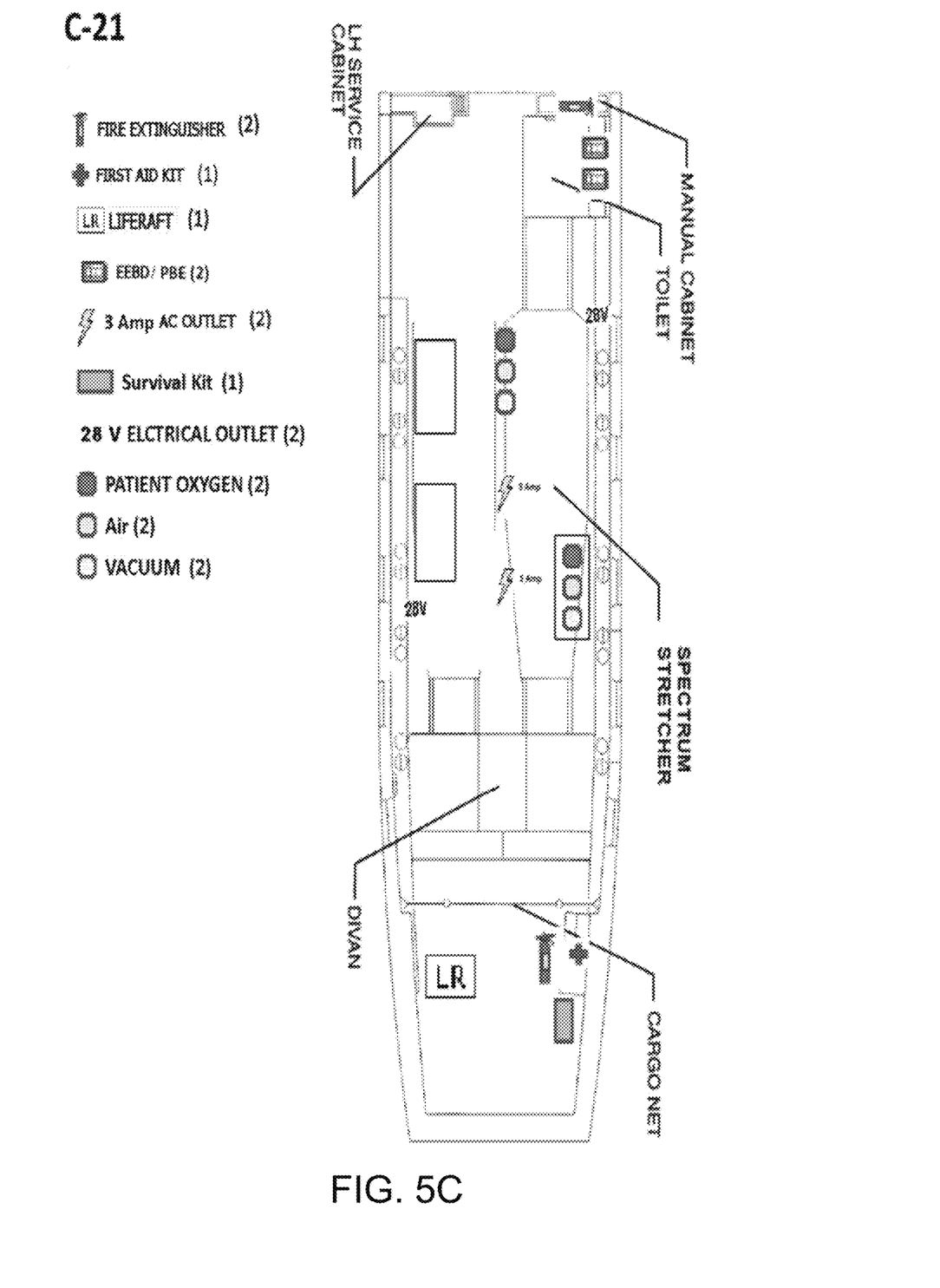
Figure 5D:
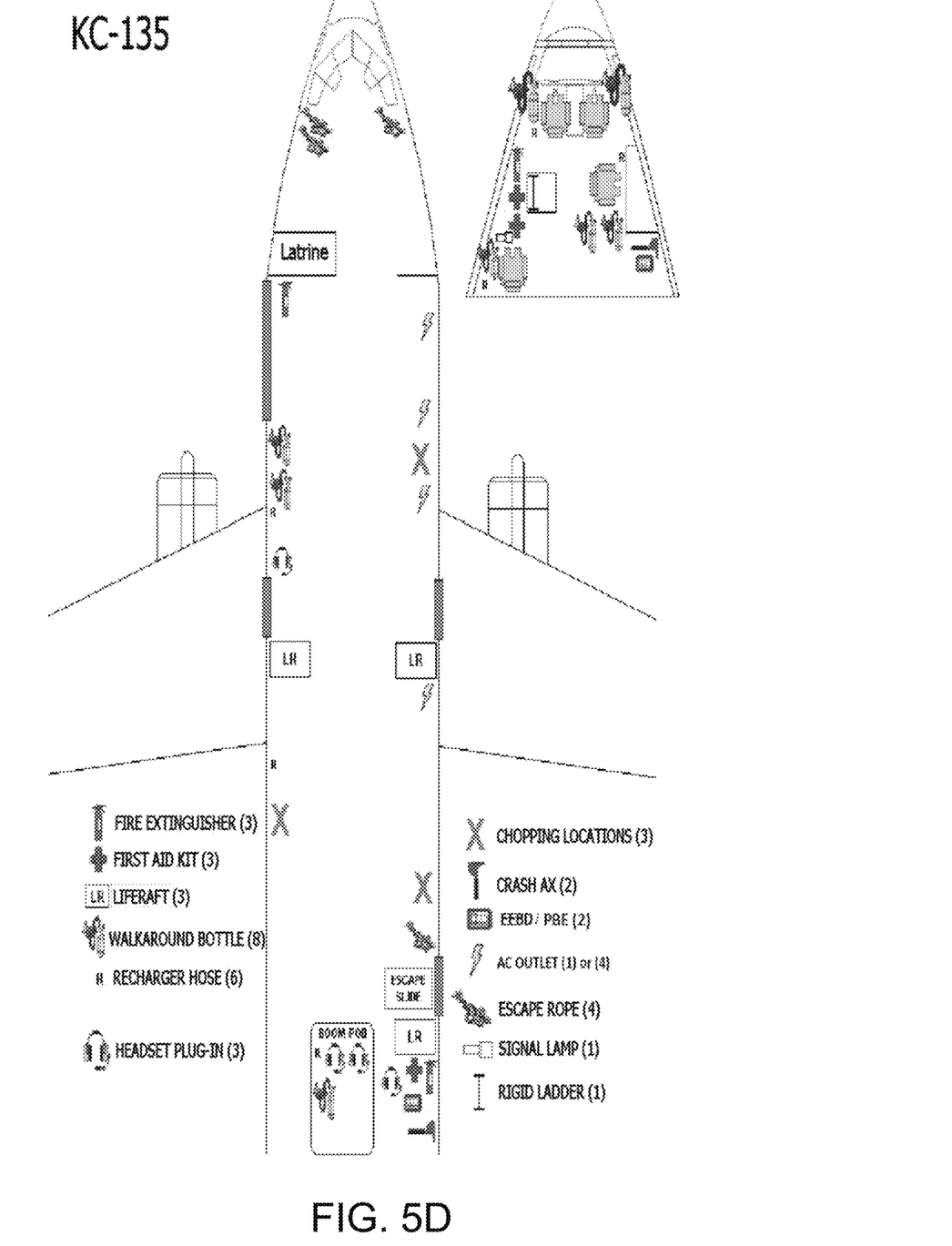

FIGS. 5A-5D depict positioning diagrams illustrating default templates of exemplary aeromedical evacuation (AE) airframes suitable for use as airlift resources for ERC missions; namely, the C-130 Hercules (FIG. 5A), the C-17 Globemaster (FIG. 5B), the C-21 (FIG. 5C), and the KC-135 Stratotanker (FIG. 5D). Other airframes such as those available from the Civil Reserve Air Fleet (CRAF) may also be used within the context of the various embodiments.

Specifically, each of a the aeromedical evacuation airframes has associated with it a default template defining/describing the locations of electrical and oxygen hook ups within the airframe, the seats and litter positions that are able to be configured within the airframe, the general/default equipment associated with the airframe and the like (e.g., such as provided by Air Force Instruction 11-2AE-3V3, CL-1 "Flying Operations", 15 Aug. 2014).

Thus, based on the available configurations of a particular airframe, users such as load managers are able to select (e.g., from a drop-down menu or other interaction) available equipment and to "place" or configure the use of such equipment throughout the airframe. Users are then able to input patient names and data and then drag and drop where they want the patients to be placed. Users are able to save load plans for future use. The system then auto calculates patient and equipment weights based on left, center, right, and pallet position, a key feature to ensure safety. This information can then be rapidly be disseminated to other aircraft personnel.

The above-described embodiments also find utility within the civilian medical field for patient placement within hospitals; specifically, patient location and medical resource allocation may be made with respect to the available resources of a non-transport platform such as a field hospital or more permanent medical facility.

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the scope of the general inventive concept.

What is claimed is:

1. A method automatically managing En Route Care (ERC) transport patient and medical equipment loading, comprising:
    transmitting, toward a load manager communications device (LMCD) associated with an ERC transport platform, a corresponding initial transport platform profile defining available transport platform resources and allocations thereof;
    in response to an LMCD message indicative of a patient selection, identifying transport platform resources for the selected patient and transmitting toward the LMCD a message indicative of the identified medical resources;
    in response to an LMCD message indicative of a loading plan update, updating the respective current transport platform profile; and
    transmitting, toward the LMCD associated with the ERC transport platform, a corresponding current transport platform profile defining available transport platform resources and allocations thereof in accordance with the current patient loading plan;
    wherein each transport platform profile transmitted toward a respective LMCD is configured to be modified by the respective LMCD to update thereby a loading plan;
    monitoring patient health parameters using monitoring equipment or sensors suitable for monitoring patient health;
    transmitting health parameter data automatically to the LMCD;
    sensing environmental conditions that impact patient health and comfort including aircraft vibration, atmospheric oxygen level changes, atmospheric pressure level changes and atmospheric temperature level changes with sensors operably coupled to the LMCD;
    wherein each transport platform profile transmitted toward a respective LMCD is configured to provide a graphical depiction of the transport platform and the available transport platform resources and allocations thereof, the graphical depiction being suitable for use by a graphical user interface (GUI) invoked at the respective LMCD;
    wherein a warning signal is displayed on the GUI when a predetermined threshold limit as measured by one or more of the sensor is exceeded; and
    wherein a modification of patient location is displayed on the GUI in response to the warning signal.

2. The method of claim 1, wherein identifying transport platform resources for the selected patient comprises examining a respective patient profile to identify therefrom at least one continuous use resource critical for survival of the selected patient.

3. The method of claim 2, wherein said at least one continuous use resource comprises any of a fluid delivery resource, a breathing resource and a cardiac monitoring resource.

4. The method of claim 2, wherein identifying transport platform resources for the selected patient further comprises examining the respective patient profile to identify therefrom at least one emergent use resource associated with the medical condition of the selected patient.

5. The method of claim 4, wherein said at least one emergent use resource comprises any of a fluid delivery resource, a breathing resource and a cardiac monitoring resource.

6. The method of claim 1, further comprising transmitting a boundary condition warning toward the LMCD in response to a loading plan update violating a boundary condition, said boundary condition comprising an allocation of an unavailable resource.

7. The method of claim 1, further comprising:
    receiving, from at least one patient health monitoring device, respective patient health information; and
    in response to patient health information associated with a change in patient location, responsively updating the transport platform load plan.

8. The method of claim 7, further comprising:
    receiving, from at least one patient location monitoring device, respective patient location information; and
    in response to change in patient location, responsively updating the transport platform load plan.

9. The method of claim 7, further comprising:
    receiving, from at least one patient environmental monitoring device, respective patient environmental information; and
    in response to patient environmental information associated with a change in patient location, responsively updating the transport platform load plan.

10. The method of claim 9, wherein the patient environmental information associated with a change in patient location comprises data indicative of patient fatigue beyond a threshold level.

11. The method of claim 1, further comprising:
    receiving, from at least one non-patient health monitoring device or environmental monitoring device, respective non-patient health information or environmental information; and
    in response to the received non-patient health information or environmental information being associated with a change in non-patient location, responsively updating the transport platform load plan.

12. The method of claim 7, further comprising:
in response to an indication of an ERC transport platform location being associated with a pathogen or having located therein a patient exhibiting symptoms of a communicable disease, using patient location information to identify any patients or non-patients exposed to that ERC transport platform location.

13. A system for automatically managing medivac transport loading, comprising:
a load management server (LMS) configured for transmitting, toward a load manager communications device (LMCD) associated with an ERC transport platform, a corresponding initial transport platform profile defining available transport platform resources and allocations thereof; and
at least one load manager communications device (LMCD) associated with the ERC transport platform and configured to receive patient and resource location information associated with a load plan for the ERC transport platform, and for generating LMCD messages in response to load plan changes;
the LMS, in response to an LMCD message indicative of a patient selection, identifying transport platform resources for the selected patient and transmitting toward the LMCD a message indicative of the identified medical resources;
the LMS, in response to an LMCD message indicative of a loading plan update, updating the respective current transport platform profile; and
the LMS transmitting, toward the LMCD associated with the ERC transport platform, a corresponding current transport platform profile defining available transport platform resources and allocations thereof in accordance with the current patient loading plan;
wherein each transport platform profile transmitted toward a respective LMCD is configured to be modified by the respective LMCD to update thereby a loading plan; and
monitoring environmental conditions with the LMCD using sensors operably coupled to the LMCD configured to record environmental factors experienced by a patient on a transport resource including at least one of pressure, temperature, vibration/shock and air quality/composition;
a graphical user interface (GUI) configured to provide a graphical depiction of the transport platform and the available transport platform resources and allocations thereof,
wherein a warning signal is displayed on the GUI when a predetermined threshold limit as measured by one or more of the sensor is exceeded; and
wherein a modification of patient location is displayed on the GUI in response to the warning signal.

14. The system of claim 13, wherein identifying transport platform resources for the selected patient comprises examining a respective patient profile to identify therefrom at least one continuous use resource critical for survival of the selected patient.

15. The system of claim 14, wherein identifying transport platform resources for the selected patient further comprises examining the respective patient profile to identify therefrom at least one emergent use resource associated with the medical condition of the selected patient.

16. The system of claim 13, wherein said LMS is further configured for transmitting a boundary condition warning toward the LMCD in response to a loading plan update violating a boundary condition, said boundary condition comprising an allocation of an unavailable resource.

17. The system of claim 13, wherein each transport platform profile transmitted toward a respective LMCD is configured to provide a graphical depiction of the transport platform and the available transport platform resources and allocations thereof, the graphical depiction being suitable for use by a graphical user interface (GUI) invoked at the respective LMCD.

18. A computer implemented method for automatically managing En Route Care (ERC) transport patient and medical equipment loading, comprising:
transmitting, toward a load manager communications device (LMCD) associated with an ERC transport platform, a corresponding initial transport platform profile defining available transport platform resources and allocations thereof;
in response to an LMCD message indicative of a patient selection, identifying transport platform resources for the selected patient and transmitting toward the LMCD a message indicative of the identified medical resources;
in response to an LMCD message indicative of a loading plan update, updating the respective current transport platform profile; and
transmitting, toward the LMCD associated with the ERC transport platform, a corresponding current transport platform profile defining available transport platform resources and allocations thereof in accordance with the current patient loading plan;
wherein each transport platform profile transmitted toward a respective LMCD is configured to be modified by the respective LMCD to update thereby a loading plan; and
displaying a current load plan of a transport resource based upon a graphical representation of the patient location and resources associated with that transport resource via a transport resource profile;
displaying a warning signal on the GUI when a sensed parameter received by a sensor is exceeds a predetermined threshold; and
automatically modifying patient location on the GUI in response to the warning signal.

19. A tangible and non-transient computer readable storage medium storing computer-executable instructions which, when executed by a system of computer processors, adapt the operation of the system to perform a method for automatically managing En Route Care (ERC) transport patient and medical equipment loading, comprising:
transmitting, toward a load manager communications device (LMCD) associated with an ERC transport platform, a corresponding initial transport platform profile defining available transport platform resources and allocations thereof;
in response to an LMCD message indicative of a patient selection, identifying transport platform resources for the selected patient and transmitting toward the LMCD a message indicative of the identified medical resources;
in response to an LMCD message indicative of a loading plan update, updating the respective current transport platform profile; and
transmitting, toward the LMCD associated with the ERC transport platform, a corresponding current transport platform profile defining available transport platform resources and allocations thereof in accordance with the current patient loading plan;

wherein each transport platform profile transmitted toward a respective LMCD is configured to be modified by the respective LMCD to update thereby a loading plan; and generating graphical imagery on a GUI associated with the transport platform profile including at least one of patient location imagery and resource location imagery suitable for use within the context of a graphical user interface generated by the LMCD for use by the load manager while forming the load plan;

displaying a warning signal on the GUI when a sensed parameter received by a sensor is exceeds a predetermined threshold; and modifying patient location on the transport to correspond with updated recommended patient location displayed the GUI in response to the warning signal.

* * * * *